(12) United States Patent
Riess et al.

(10) Patent No.: US 10,828,436 B2
(45) Date of Patent: Nov. 10, 2020

(54) ADMINISTERING THE NOBLE GAS ARGON DURING CARDIOPULMONARY RESUSCITATION

(71) Applicant: Vanderbilt University, Nashville, TN (US)

(72) Inventors: Matthias L. Riess, Nashville, TN (US); Demetris Yannopoulos, Minneapolis, MN (US); Tom P. Aufderheide, Milwaukee, WI (US)

(73) Assignees: Vanderbilt University, Nashville, TN (US); Medical College of Wisconsin, Milwaukee, WI (US)

( * ) Notice: Subject to any disclaimer, the term of this patent is extended or adjusted under 35 U.S.C. 154(b) by 446 days.

(21) Appl. No.: 15/480,280

(22) Filed: Apr. 5, 2017

(65) Prior Publication Data

US 2017/0312460 A1 Nov. 2, 2017

Related U.S. Application Data

(60) Provisional application No. 62/318,759, filed on Apr. 5, 2016.

(51) Int. Cl.
*A61M 16/00* (2006.01)
*A61K 41/00* (2020.01)
(Continued)

(52) U.S. Cl.
CPC .............. *A61M 16/00* (2013.01); *A61K 9/007* (2013.01); *A61K 41/0004* (2013.01); *A61M 16/0003* (2014.02); *A61M 16/12* (2013.01); *A61H 31/00* (2013.01); *A61H 2201/5071* (2013.01); *A61H 2230/205* (2013.01); *A61H 2230/207* (2013.01);
(Continued)

(58) Field of Classification Search
CPC .............. A61M 16/00; A61M 16/0003; A61M 16/0048; A61M 16/0057; A61M 16/0078; A61M 16/0084; A61M 16/01; A61M 16/12; A61M 15/00; A61M 2202/02; A61M 2202/0208; A61M 2202/025; A61M 2202/0258; A61M 2202/0291; A61N 1/3904; A61N 1/39044; A61H 31/00
See application file for complete search history.

(56) References Cited

U.S. PATENT DOCUMENTS 9,101,556 B2 * 8/2015 Kobayashi ............. A61K 33/00
2003/0178025 A1 * 9/2003 Holt ..................... A61H 31/007
128/205.13
(Continued)

OTHER PUBLICATIONS

Smit KF, Weber NC, Hollmann MW, Preckel B. Noble gases as cardioprotectants—translatability and mechanism. Br J Pharmacol. 2015;172(8):2062-73.; retrieved from https://www.ncbi.nlm.nih.gov/pmc/articles/PMC4386981/ (Year: 2015).*

(Continued)

*Primary Examiner* — Joseph D. Boecker
(74) *Attorney, Agent, or Firm* — Stites & Harbison PLLC; Sean P. Ritchie

(57) ABSTRACT

Method of treating an individual following a period of ischemia are provided. The methods include administering inhaled agents postconditioning to the individual and optionally simultaneously performing cardiopulmonary resuscitation. The inhaled agents include at least one noble gas.

19 Claims, 8 Drawing Sheets

(51) Int. Cl.
  *A61M 16/12* (2006.01)
  *A61H 31/00* (2006.01)
  *A61K 9/00* (2006.01)
(52) U.S. Cl.
  CPC ..... *A61H 2230/42* (2013.01); *A61M 16/0078* (2013.01); *A61M 2202/02* (2013.01); *A61M 2202/025* (2013.01); *A61M 2202/0208* (2013.01); *A61M 2202/0258* (2013.01); *A61M 2205/05* (2013.01); *A61M 2230/40* (2013.01)

(56) References Cited

U.S. PATENT DOCUMENTS

| | | | | |
|---|---|---|---|---|
| 2009/0020127 | A1* | 1/2009 | Boone | A61M 16/0051 128/207.14 |
| 2009/0311340 | A1* | 12/2009 | Franks | A61K 31/08 424/600 |
| 2010/0051025 | A1* | 3/2010 | Zapol | A61K 33/00 128/203.12 |
| 2014/0048061 | A1* | 2/2014 | Yannopoulos | A61H 31/00 128/200.14 |
| 2014/0363391 | A1* | 12/2014 | Yannopoulos | A61K 31/77 424/78.3 |
| 2016/0199406 | A1* | 7/2016 | Schmidt | A61K 31/08 424/708 |
| 2016/0213879 | A1* | 7/2016 | Parthasarathy | A61M 16/208 |

OTHER PUBLICATIONS

Cleland, Marshall & Galloway, Richard. (2015). Ozone Generation in Air during Electron Beam Processing. Physics Procedia. 66. 586-594. 10.1016/j.phpro.2015.05.078 (Year: 2015).*
Nichol G, Soar J: Regional cardiac resuscitation systems of care. Curr Opin Crit Care 2010; 16: 223-30. PMID: 20463465.
Böttiger BW, Van Aken HK: Saving 100,000 lives each year in Europe. Best Pract Res Clin Anaesthesiol 2013; 27: 291-2. PMID: 24054507.
Kalogeris T, Bao Y, Korthuis RJ: Mitochondrial reactive oxygen species: a double edged sword in ischemia/reperfusion vs preconditioning. Redox Biol 2014; 2: 702-14. PMID: 24944913.
Zhao ZQ et al. Inhibition of myocardial injury by ischemic postconditioning during reperfusion: Comparison with ischemic preconditioning. Am J Physiol Heart Circ Physiol. 2003;285:H579-588.
Zhao H. Ischemic postconditioning as a novel avenue to protect against brain injury after stroke. J Cereb Blood Flow Metab. 2009;29:873-885.
Bernard SA, et al. Treatment of comatose survivors of out-of-hospital cardiac arrest with induced hypothermia. N Engl J Med. 2002;346:557-563.
Segal N, Matsuura T, Caldwell E, Sarraf M, McKnite S, Zviman M, Aufderheide TP, Halperin HR, Lurie KG, Yannopoulos D: Ischemic postconditioning at the initiation of cardiopulmonary resuscitation facilitates functional cardiac and cerebral recovery after prolonged untreated ventricular fibrillation. Resuscitation 2012; 83: 1397-403. PMID: 22521449.
Graham, et al.,; Strategies to Improve Cardiac Arrest Survival: A Time to Act. Institute of Medicine 2015, pp. 1-4.
Aufderheide TP, et al. Standard cardiopulmonary resuscitation versus active compression-decompression cardiopulmonary resuscitation with augmentation of negative intrathoracic pressure for out-of-hospital cardiac arrest: A randomised trial. Lancet. 2011;377:301-311.
Yellon DM, et al. Myocardial reperfusion injury. N Engl J Med. 2007;357:1121-1135.
Staat P, et al. Postconditioning the human heart. Circulation. 2005;112:2143-2148.
Gateau-Roesch O, et al. Mitochondrial permeability transition pore and postconditioning. Cardiovasc Res. 2006;70:264-273.
Murphy E, et al. What makes the mitochondria a killer? Can we condition them to be less destructive? Biochim Biophys Acta. 2011;1813:1302-1308.
Piot C, et al. Effect of cyclosporine on reperfusion injury in acute myocardial infarction. N Engl J Med. 2008;359:473-481.
Cour M, et al. Inhibition of mitochondrial permeability transition to prevent the post-cardiac arrest syndrome: A pre-clinical study. Eur Heart J. 2011;32:226-235.
Chen D, et al. The effect of sevoflurane postconditioning on cardioprotection against ischemia-reperfusion injury in rabbits. Mol Biol Rep. 2012;39:6049-6057.
Meybohm P, et al. Pharmacological postconditioning with sevoflurane after cardiopulmonary resuscitation reduces myocardial dysfunction. Crit Care. 2011;15:R241.
Rohilla A, et al. Myocardial postconditioning: Next step to cardioprotection. Arch Pharm Res. 2011;34:1409-1415.
Oei GT, et al. Cellular effects of helium in different organs. Anesthesiology. 2010;112:1503-1510.
Wang JK, et al. Postconditioning with sevoflurane protects against focal cerebral ischemia and reperfusion injury via pi3k/akt pathway. Brain Res. 2010;1357:142-151.
Meybohm P, Gruenewald M, Albrecht M, Müller C, Zitta K, Foesel N, Maracke M, Tacke S, Schrezenmeir J, Scholz J, Bein B: Pharmacological postconditioning with sevoflurane after cardiopulmonary resuscitation reduces myocardial Dysfunction. Crit Care 2011; 15: R241. PMID: 22011328.
Riess ML, Matsuura TR, Bartos JA, Bienengraeber M, Aldakkak M, McKnite SH, Rees JN, Aufderheide TP, Sarraf M, Neumar RW, Yannopoulos D: Anaesthetic Postconditioning at the Initiation of CPR Improves Myocardial and Mitochondrial Function in a Pig Model of Prolonged Untreated Ventricular Fibrillation. Resuscitation 2014; 85: 1745-51. PMID: 25281906.
Bartos JA, Matsuura TR, Sarraf M, Youngquist ST, McKnite SH, Rees JN, Sloper DT, Bates FS, Segal N, Debaty G, Lurie KG, Neumar RW, Metzger JM, Riess ML, Yannopoulos D: Bundled postconditioning therapies improve nemodynamics and neurologic recovery after 17 min of untreated cardiac arrest Resuscitation 2015; 87: 7-13. PMID: 25447036.
Brücken A, Cizen A, Fera C, Meinhardt A, Weis J, Nolte K, Rossaint R, Pufe T, Marx G, Fries M: Argon reduces neurohistopathological damage and preserves functional recovery after cardiac arrest in rats. Br J Anaesth 2013; 110 Suppl 1: i106-12. PMID: 23393152.
Brücken A, Kumaz P, Bleilevens C, Derwall M, Weis J, Nolte K, Rossaint R, Fries M: Dose dependent neuroprotection of the noble gas argon after cardiac arrest in rats is not mediated by KATP-channel opening. Resuscitation 2014; 85: 826-32. PMID: 24582739.
Ristagno G, Fumagalli F, Russo I, Tantillo S, Zani DD, Locatelli V, De Maglie M, Novelli D, Staszewsky L, Vago T, Belloli A, Di Giancamillo M, Fries M, Masson S, Scanziani E, Latini R: Postresuscitation treatment with argon improves early neurological recovery in a porcine model of cardiac arrest. Shock 2014; 41:72-8. PMID: 24088999.
Pagel PS: Cardioprotection by noble gases. J Cardiothorac Vasc Anesth 2010; 24: 143-63. PMID: 19467886.
Schultz J, et al. Sodium nitroprusside enhanced cardiopulmonary resuscitation prevents post-resuscitation left ventricular dysfunction and improves 24-hour survival and neurological function in a porcine model of prolonged untreated ventricular fibrillation. Resuscitation. 2011;82S:S35-S40.
Shaffner DH, et al. Effect of arrest time and cerebral perfusion pressure during cardiopulmonary resuscitation on cerebral blood flow, metabolism, adenosine triphosphate recovery, and ph in dogs. Crit Care Med. 1999;27:1335-1342.
Allen BS, et al. Studies of isolated global brain ischaemia: Ii. Controlled reperfusion provides complete neurologic recovery following 30 min of warm ischaemia—the importance of perfusion pressure. Eur J Cardiothorac Surg. 2012;41:1147-1154.
Segal N, et al. Ischemic postconditioning at the initiation of cardiopulmonary resuscitation facilitates functional cardiac and cerebral recovery after prolonged untreated ventricular fibrillation. Resuscitation. 2012.
Yannopoulos D, et al. Controlled pauses at the initiation of sodium nitroprusside-enhanced cardiopulmonary resuscitation facilitate neu-

(56) References Cited

OTHER PUBLICATIONS rological and cardiac recovery after 15 mins of untreated ventricular fibrillation. Crit Care Med. 2012;40:1562-1569.

Högler S, et al. Distribution of neuropathological lesions in pig brains after different durations of cardiac arrest. Resuscitation. 2010;81:1577-1583.

Riess ML, et al. Preconditioning with sevoflurane reduces changes in nicotinamide adenine dinucleotide during ischemia-reperfusion in isolated hearts: Reversal by 5-hydroxydecanoic acid. Anesthesiology. 2003;98:387-395.

Kevin LG, et al. Sevoflurane exposure generates superoxide but leads to decreased superoxide during ischemia and reperfusion in isolated hearts. Anesth Analg. 2003;96:949-955, table of contents.

Siman R, et al. Novel surrogate markers for acute brain damage: Cerebrospinal fluid levels corrrelate with severity of ischemic neurodegeneration in the rat J Cereb Blood Flow Metab. 2005;25:1433-1444.

Che D, et al. Impact of therapeutic hypothermia onset and duration on survival, neurologic function, and neurodegeneration after cardiac arrest. Crit Care Med. 2011;39:1423-1430.

Griffiths C, et al. A new and simple method for delivering clamped nitric oxide concentrations in the physiological range: Application to activation of guanylyl cyclase-coupled nitric oxide receptors. Mol Pharmacol. 2003;64:1349-1356.

McAllister SE, et al. Postconditioning for salvage of ischemic skeletal muscle from reperfusion injury: Efficacy and mechanism. Am J Physiol Regul Integr Comp Physiol. 2008;295:R681-689.

Stumpner J, et al. Desflurane-induced post-conditioning against myocardial infarction is mediated by calcium-activated potassium channels: Role of the mitochondrial permeability transition pore. Br J Anaesth. 2012;108:594-601.

Tsang A, et al. Myocardial postconditioning: Reperfusion injury revisited. Am J Physiol Heart Circ Physiol. 2005;289: H2-7.

Becker LB. New concepts in reactive oxygen species and cardiovascular reperfusion physiology. Cardiovasc Res. 2004;61:461-470.

Penna C, et al. Mitochondrial pathways, permeability transition pore, and redox signaling in cardioprotection: Therapeutic implications. Antioxid Redox Signal. 2012.

Lu Z, et al. Extracellular superoxide dismutase deficiency exacerbates pressure overload-induced left ventricular hypertrophy and dysfunction. Hypertension. 2008;51:19-25.

Zhang P, et al. Nadph oxidase contributes to coronary endothelial dysfunction in the failing heart. Am J Physiol Heart Circ Physiol. 2009;296:H840-846.

Aldakkak M, et al. Ranolazine reduces ca2+ overload and oxidative stress and improves mitochondrial integrity to protect against ischemia reperfusion injury in isolated hearts. Pharmacol Res. 2011;64:381-392.

Gadicherla AK, et al. Damage to mitochondrial complex i during cardiac ischemia reperfusion injury is reduced indirectly by antianginal drug ranolazine. Biochim Biophys Acta. 2012;1817:419-429.

Heinen A, et al. Reverse electron flow-induced ros production is attenuated by activation of mitochondrial ca2+-sensitive k+ channels. Am J Physiol Heart Circ Physiol. 2007;293:H1400-1407.

\* cited by examiner

70% Argon / 30% O$_2$

70% Nitrogen / 30% $O_2$
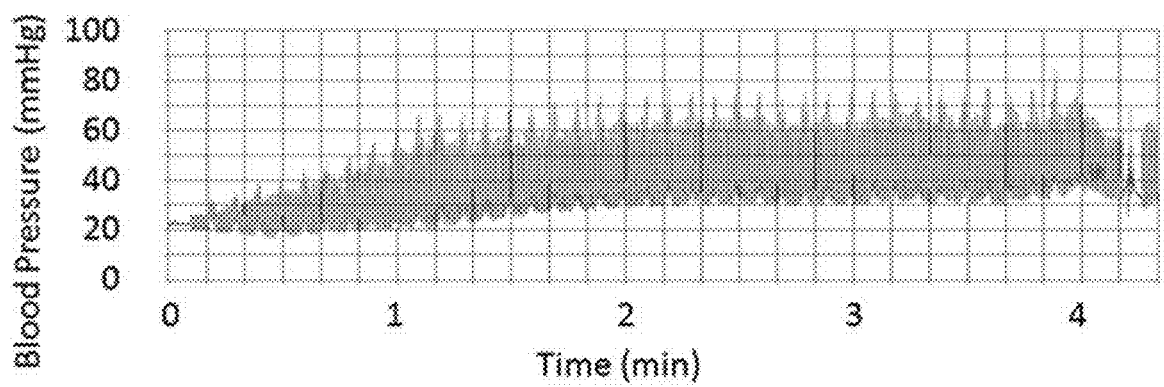
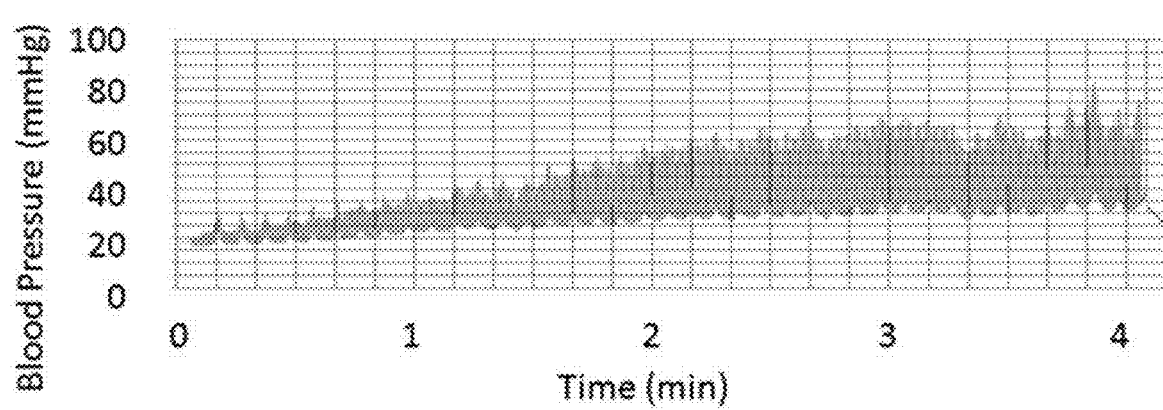
Figure 8, cont'd

ADMINISTERING THE NOBLE GAS ARGON DURING CARDIOPULMONARY RESUSCITATION

RELATED APPLICATIONS

This application claims the benefit of U.S. Provisional Application Ser. No. 62/318,759, filed Apr. 5, 2016, the entire disclosure of which is incorporated herein by this reference.

GOVERNMENT INTEREST

This invention was made with government support under grant number R01 HL095122 awarded by the National Institutes of Health. The government has certain rights in the invention.

TECHNICAL FIELD

The presently-disclosed subject matter generally relates to reducing reperfusion injury in tissues following an ischemic event. In particular, certain embodiments of the presently-disclosed subject matter relate to the administration of a noble gas while performing cardiopulmonary resuscitation on an individual in need thereof before the return of spontaneous circulation.

BACKGROUND

Cardiac arrest (CA) continues to be a leading cause of death worldwide. Each year, more than 300,000 patients in the US alone are victims of out-of-hospital cardiac arrest (OHCA). Successful CPR and outcomes are inversely proportional to the duration of untreated arrest. Unfortunately, 60-80% of patients with OHCA do not receive bystander CPR, and first responders (police, firefighters, paramedics) arrive on average 8-10 min after the 911 call. In these patients, the molecular and metabolic changes that result from abrupt reperfusion (reintroduction of blood flow during the initiation of CPR) after prolonged systemic ischemia may be of greater consequence than the injury caused by the duration of initial ischemia itself.

Even with the best cardiopulmonary resuscitation (CPR), more than 90% suffer severe neurological deficits or die. According to the Institute of Medicine report "Strategies to Improve Cardiac Arrest Survival: A Time to Act", there is a "national responsibility . . . to improve the likelihood of survival and favorable neurologic outcomes following cardiac arrest." Paradoxically, reintroduction of blood flow after prolonged untreated CA is thought to contribute significantly to overall ischemia/reperfusion (IR) injury, so strategies to reduce IR injury upon reperfusion are desperately needed.

Over the last half century, despite extensive research, only a relatively small improvement in resuscitation survival outcomes has been observed. Although reperfusion injury (RI) is a well-established concept in the cardiology, neurology, and transplant literature, there is a notable lack of research investigating the relevance of RI, and potential strategies to protect against it, in the CPR literature. Most efforts have focused on improving hemodynamics during CPR. Work by numerous investigators (including our group) has shown that by improving the quality of CPR and by optimizing blood flow, survival outcomes can be improved, but only marginally. In response to such research, the resuscitation community has focused on bystander CPR, emphasizing the practice of high-quality compressions (adequate rate, depth, compression fraction), early defibrillation, and the elimination of relative hyperventilation and incomplete decompressions.

Outside of CPR, one critical contribution to the field was identification of the value of post cardiac arrest therapeutic hypothermia (TH). At the time, TH was the only therapy besides very early defibrillation to improve neurologically intact survival. Use of TH introduced the notion of cerebral protection, albeit late in the resuscitation process. Unfortunately, TH has only been shown to be beneficial in resuscitated patients with VF, which is present in less than 30% of patients presenting with OHCA. Moreover, even in the best emergency medical systems, only 40-50% of these patients have successful return of spontaneous circulation (ROSC). Thus, only a very small proportion of OHCA patients benefit from TH.

Another approach for treating RI includes controlling reintroduction of blood flow after prolonged ischemia. One example includes ischemic postconditioning (IPC), or intermittent ischemia that is applied at the initiation of reperfusion after a prolonged ischemic event. There is evidence that IPC is advantageous for cardiac muscle protection after ischemia. IPC has been shown to offer cardiac and cerebral protection after focal (individual organ) ischemic insults such as ST elevation myocardial infarction and ischemic stroke. Other data show a benefit of IPC with controlled reperfusion in preventing RI in most organs including the brain, liver, kidney, retina, and small intestine. This simple yet critical alteration in reintroducing blood flow after an ischemic insult has been effectively applied as a clinical therapy to preserve and restore organ function in models of myocardial infarction, transplantation, and stroke. However, to date, no IPC strategy has been developed and evaluated for OHCA patients or other forms of cardiac arrest (the ultimate model of global ischemia).

An additional approach for attenuating ischemia/reperfusion (IR) injury includes pharmacologic postconditioning. For example, it may be possible to attenuate IR injury by administering cyclosporine A, an mPTP inhibitor. However, RI occurs very early during re-introduction of blood flow. Because intravenous drugs are dependent on intravenous access by late arriving ACLS providers, and because these drugs lose their benefit when organs are reperfused more than 3 min before their administration, they have limited applicability in cardiac arrest.

As an alternative to intravenous drugs, a recent study showed that delayed postconditioning with a volatile anesthetic, such as sevoflurane, when given by inhalation after resuscitation, may provide improved hemodynamic outcomes in animals without relying upon intravenous access. For example, patents WO2014026193 A1 and US20140048061 A1 describe the administration of various intravenous and inhaled anesthetic drugs to improve outcome after cardiac arrest and CPR when administered during CPR. Volatile anesthetics are considered to provide protection from RI. Although the mechanisms are not fully elucidated, there is evidence that they involve protein kinase B and glycogen synthase kinase 3 beta activation, as well as protection of mitochondrial membrane integrity and prevention of cell death.

In the case of sevoflurane postconditioning, current evidence suggests that cardioprotection is maximized by administration of an end-tidal concentration of 2.4 vol. % for the first 2 min of reperfusion. This very short application effectively protects the heart against RI in rats in vivo; in contrast, a longer administration seems to offer less protection while accentuating its cardiodepressant side-effects. Safe administration of volatile anesthetics outside the operating room or intensive care unit, however, is complicated by their anesthetic effect and potential harm to providers and bystanders through room air contamination.

Accordingly, there remains a need in the art for articles and methods for safely and effectively improving outcomes following cardiac arrest.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of treating an individual following a period of ischemia, the method comprising administering inhaled agents postconditioning, the inhaled agents comprising at least one noble gas. In one embodiment, the inhaled agent is selected from the group consisting of argon, helium, and a combination thereof. In another embodiment, the inhaled agent includes a pure noble gas or a mixture of at least one noble gas and oxygen. In a further embodiment, the mixture of the at least one noble gas and oxygen includes a noble gas:oxygen ration of 80:20, 70:30, 60:40, or 50:50. The inhaled agent postconditioning may be administered within 15 minutes of the period of ischemia, at least 10 minutes after the period of ischemia, or at least 15 minutes after the period of ischemia.

In some embodiments, the method further includes simultaneously performing cardiopulmonary resuscitation. In one embodiment, the cardiopulmonary resuscitation comprises at least one intentional pause in chest compression. In another embodiment, treating the individual includes reducing reperfusion injury following the period of ischemia.

In some embodiments, the presently disclosed subject matter includes a method to reduce injury of cells after a period of ischemia the method comprising administering inhaled agents postconditioning and simultaneously performing cardiopulmonary resuscitation. In one embodiment, the cells are myocardial cells. In another embodiment, the cells are neuronal cells.

In some embodiments, the presently disclosed subject matter includes a method performing cardiopulmonary resuscitation to an individual comprising repeatedly compressing an individual's chest, wherein the chest is compressed during a compression phase followed by a decompression or relaxation phase, and administering inhaled agent postconditioning to the individual receiving cardiopulmonary resuscitation. The cardiopulmonary resuscitation comprises at least one intentional pause in chest compression. In one embodiment, the inhaled agent comprises at least one noble gas.

Further features and advantages of the presently-disclosed subject matter will become evident to those of ordinary skill in the art after a study of the description, figures, and non-limiting examples in this document.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
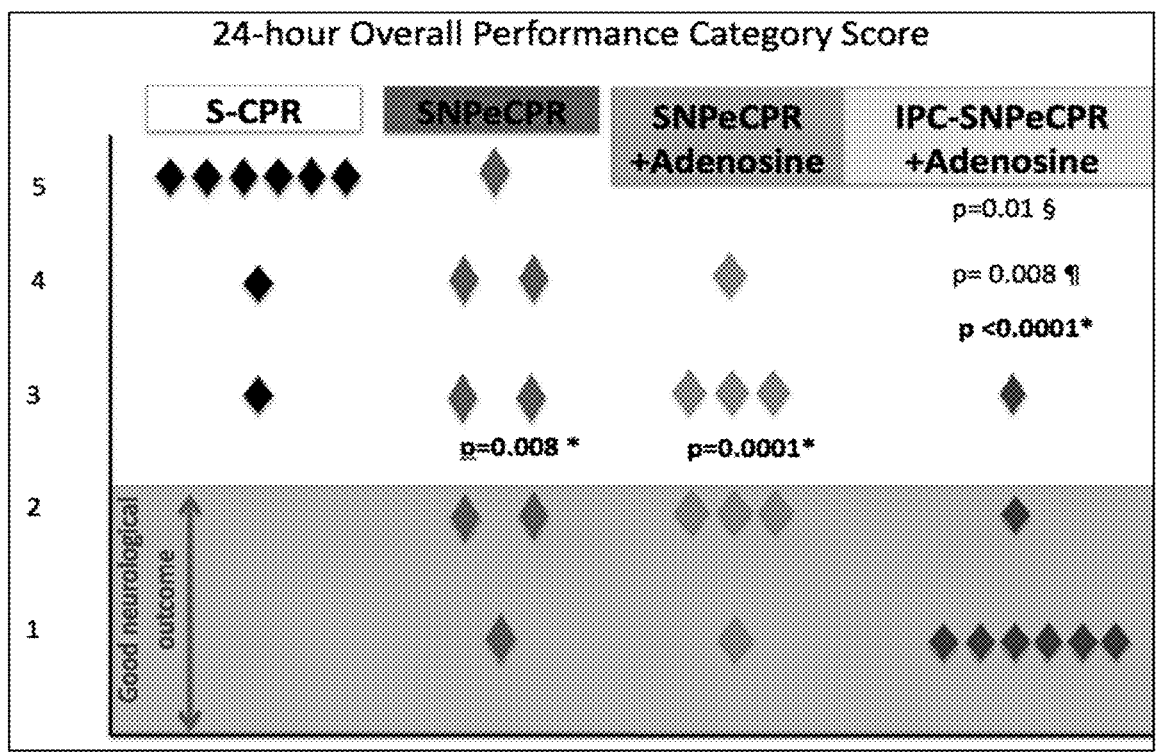
FIG. 1 shows that after 15 min of untreated ventricular fibrillation (VF), when IPC (with four 20-second pauses in compressions and ventilations) was added on SNPeCPR+ Adenosine, 6/8 animals were blinded scored as normal (CPC of 1). *¶ § mean statistically significant difference compared to (standard) S-CPR, SNPeCPR and SNPeCPR+adenosine respectively.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, databases, websites and other published materials referred to throughout the entire disclosure herein, unless noted otherwise, are incorporated by reference in their entirety.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes compounds and methods for treating individuals following an ischemic event and/or reducing reperfusion injury (RI) in tissues following an ischemic event. In some embodiments, the methods include pharmacological postconditioning, such as inhaled agents postconditioning (IAPC). IAPC includes administering an inhaled agent to an individual following an ischemic event. In one embodiment, the inhaled agent includes one or more noble gases. As used herein, the term "noble gas" refers to helium (He), neon (Ne), argon (Ar), krypton (Kr), xenon (Xe), radon (Rn), and oganesson (Og), the seven chemical elements that make up Group 18 (VIIIa) of the periodic table. For example, in another embodiment, the inhaled agent in IAPC includes one or more of argon and helium. Additionally or alternatively, the inhaled agent may be limited to non-anesthetic noble gases, such as helium (He), neon (Ne), argon (Ar), krypton (Kr), radon (Rn), and/or oganesson (Og). In this regard, it is noted that while xenon is a useable anesthetic at elevated concentration (e.g., 80% or more) and normal atmospheric pressure, other noble gases may become anesthetics under hyperbaric conditions. As such, the term non-anesthetic noble gases refers not only to the gases listed above, but also to such gases under normal (i.e., non-hyperbaric) conditions.

IAPC may be administered immediately after an ischemic event and/or subsequent to an ischemic event. For example, in one embodiment, IAPC is administered within the first 2 to 3 minutes of an ischemic event, within 5 minutes, within 10 minutes, and/or within 15 minutes. In another embodiment, IAPC may be administered 15 or more minutes after the ischemic event. In a further embodiment, IAPC is administered at an initial phase of reperfusion, during cardiopulmonary resuscitation (CPR), and/or before the return of spontaneous circulation (ROSC). Additionally or alternatively, the administering of the inhaled agent following an ischemic event may include administering pure noble gases/non-anesthetic noble gases or a mixture including one or more noble gases/non-anesthetic noble gases and any other suitable gas. For example, in some embodiments, the inhaled agent is provided as a noble gas/non-anesthetic noble gas and oxygen mixture. Suitable noble gas/non-anesthetic noble gas and oxygen mixtures include, but are not limited to, noble gas/non-anesthetic noble gas:oxygen ratios of 50:50, 60:40, 70:30, 80:20, and/or 90:10.

In certain embodiments, the IAPC according to one or more of the embodiments disclosed herein attenuates ischemic/reperfusion (IR) injury to vital organs and/or improves outcome and survival following cardiac arrest and CPR. For example, IAPC may protect against RI of the brain, decrease brain oxidative injury, enhance immunity indices in cerebral IR, protect ischemic kidneys, and/or provide RI protection in a variety of other organs. Accordingly, in some embodiments, IAPC provides RI protection for the multi-organ ischemia and systemic absence of blood flow during VF followed by generalized reperfusion. Without wishing to be bound by theory, it is believed that the use of noble gases, and in particular non-anesthetic noble gases, in IAPC as described herein (e.g., following cardiac arrest (CA) or other ischemic event and at an initial phase of reperfusion, during cardiopulmonary resuscitation (CPR), and/or before ROSC) improves hemodynamics and blood supply to critical organs during external chest compressions, improves rate and time of ROSC, and/or improves neurologically favorable survival.

In contrast to the limited applicability of intravenous drugs, which require intravenous access, IAPC provides immediate delivery via the airways. Delivery via the airways may be provided by any suitable method, including, but not limited to, access to the lungs through a face mask, a bag-valve-mask system, an endotracheal tube, a supraglottic airway device, or any other suitable device. In some embodiments, delivery via the airways provides earlier and/or stronger protective effects on vital organs as compared to the delayed administration of intravenous drugs.

Again, without wishing to be bound by theory, it is believed that despite their lack of chemical reactivity due to completely filled outer electron orbitals, noble gases can interact with essential signaling proteins, ion channels, and receptors to protect cardiac and neural tissue from IR injury similarly to volatile anesthetics. However, IAPC with non-anesthetic noble gases provides one or more of the benefits disclosed herein without the negative effects associated with volatile anesthetics (e.g., sevoflurane), such as, but not limited to, anesthetic, cardiodepressant, and other side-effects. Noble gases and non-anesthetic noble gases in IAPC also decrease or eliminate the negative effects of volatile anesthetics and other anesthetics on providers and bystanders, permitting the use of IAPC with noble gases/non-anesthetic noble gases outside of a hospital setting, without an elaborate scavenging system, and/or during CPR.

Additionally, in contrast to anesthetic gases, which currently only anesthesiologists, and in some states certified registered nurse anesthetists (CRNAs), are licensed to administer, noble gases may be administered by non-anesthesiologists and non-CRNAs. This permits administration by a much larger group of individuals, including those outside the operating room such as first responders and many others who may be providing CPR. Accordingly, one or more of the embodiments described herein provide the potential to transform resuscitation practice and significantly improve survival and clinical outcomes for one of the most challenging public health problems in the western world.

In some embodiments, the methods disclosed herein also include ischemic postconditioning (IPC). In one embodiment, IPC includes controlled pauses of blood flow by intermittently stopping chest compressions. In another embodiment, IPC during CPR can be provided by intentionally pausing chest compressions and ventilations during the initiation of resuscitation efforts. In a further embodiment, the intentional pauses include, but are not limited to, three to five pauses of flow (varying from 15 seconds to 1 minute) during the initial reperfusion.

The intentional pauses of IPC in the early portions of the resuscitative period are distinct from the prolonged periods of intermittent pauses of various durations characteristic of poor quality CPR, as well as periods of continuous low flow during CPR. For example, while unintentional pauses in chest compressions spread throughout resuscitative efforts and continuous low flow during CPR are associated with worse outcomes by reducing coronary and cerebral perfusion pressure, thereby adding to the injury that occurred during the no-flow period, the intentional pauses restricted to the earliest portion of the resuscitative period described herein facilitate endogenous processes associated with specific mitochondrial protective mechanisms.

Without wishing to be bound by theory, it is believed that after prolonged untreated arrest, reintroduction of blood flow contributes significantly to the overall tissue damage. However, the on/off flow strategy of IPC provides a mechanistic advantage that attenuates reperfusion injury at the initiation of CPR, reduces overall tissue damage, and/or improves overall outcome. For example, in one embodiment, three to five pauses of flow (varying from 15 seconds to 1 minute) during the initial reperfusion following an acute myocardial infarction significantly decreased infarct size in animals and humans. Accordingly, in some embodiments, combining IPC with IPAC further limits, decreases, or eliminates critical organ RI that may occur during the initiation of CPR. In this regard, IPC may be administered prior to, concurrently with, and/or subsequent to IAPC. For example, in one embodiment, IAPC is administered prior to CPR and/or IPC. In another embodiment, IAPC is administered concurrently with CPR and/or IPC. In a further embodiment, IAPC is administered subsequent to CPR and/or IPC.

In certain embodiments, IPC and/or IPAC may be combined with current methods of resuscitation. Both when combined with current methods and when provided separately, IPC and/or IPAC are readily available for application within the first 2-3 min of CPR, are simple to perform, and cause no delay in the initiation of chest compressions. Accordingly, in some embodiments, one or more of the methods disclosed herein include administering IPC and/or IPAC to an individual in need thereof within the limited window of opportunity for treating/mitigating RI (i.e., 2-3 min from the re-introduction of blood flow). Additionally, one or more of the methods disclosed herein permit administration in the field under a wide variety of conditions, with or without automated CPR devices.

In contrast to existing methods that did not provide favorable neurological outcome following prolonged systemic ischemia (e.g., 10 or more minutes from 911 call to CPR), such as the instant inventor's novel combination of non-invasive technologies that modulate intrathoracic pressures, one or more of the methods disclosed herein provide improved neurological outcomes for individuals who experience prolonged systemic ischemia and/or those whose prognosis is poor with current state-of-the-art CPR approaches. For example, in one embodiment, the use of IPC and IAPC during the initiation of CPR in a porcine model of prolonged (e.g., 15 or more minutes) untreated ventricular fibrillation (VF) cardiac arrest mitigates and/or eliminates myocardial dysfunction and cerebral RI. In another embodiment, with IPC, survival with favorable neurological function in a porcine model increased to more than 80%, demonstrating the enormous potential for full recovery even after prolonged CA and global whole body ischemia. Additionally or alternatively, in some embodiments, the methods described herein provide direct mitochondrial protection, functional salvage, individual vital organ protection, and/or clinically important functional outcomes. Furthermore, without wishing to be bound by theory, it is believed that IPC and/or IAPC provide a protective effect both in the presence and absence of bystander CPR following an ischemic event.

Thus, although current standard-of-care CPR techniques emphasize immediate and uninterrupted chest compression and limit the importance of ventilations, at least initially, the intentional introduction of pauses during CPR and/or use of inhaled agent postconditioning (IAPC) disclosed herein provide improved outcomes, including, but not limited to, protection against RI and/or neurologically intact survival. Additionally or alternatively, IPC and/or IAPC may have a synergistic effect when combined with post-resuscitation mild therapeutic hypothermia (TH).

The presently disclosed subject-matter also includes a kit for reducing reperfusion injury in tissues following an ischemic event. In some embodiments, the kit includes a defibrillator and a supply of pressurized noble gas/non-anesthetic noble gas. The supply of pressurized noble gas/non-anesthetic noble gas may include one or more pure noble gases/non-anesthetic noble gases or a mixture of one or more noble gases/non-anesthetic noble gases and another gas, such as oxygen.

The presently-disclosed subject matter is further illustrated by the following specific but non-limiting examples.

EXAMPLES

In one example, in-vivo experiments included a systematic study of the effect of Argon administered during CPR in a pig model of cardiac arrest on cardiac and neurological function, histological and other molecular effects after ROSC including 24- or 48 hr survival studies. These in-vivo experiments in pigs undergoing cardiac arrest and CPR with 70% Argon showed much improved outcome parameters compared to control animals that did not receive Argon during CPR. Other examples include cell culture (in vitro) and isolated heart (ex vivo) experiments. The in vitro experiments include a systematic study of the effect of Argon administered on reoxygenation after prolonged hypoxia on markers of cellular injury and cell death in cardiomycetes and neuronal cell cultures. The ex vivo experiments include a systematic study of the effect of Argon administered on reperfusion after global coronary ischemia on coronary and myocardial function and infarct size in rat isolated hearts.

Example 1

Neurologic Benefit of IPC (During First 3 Min of Sodium Nitroprusside "Enhanced" CPR (SNPeCPR).

In recent work, the instant inventors demonstrated the ability to provide consistent resuscitation and 24-hr survival in more than 90% of animals treated with SNP-enhanced CPR after 15 min of untreated cardiac arrest. That result had not been possible previously. However, a gap of about 40-50% between overall survival and neurologically intact survival at 24 hrs was also identified. In subsequent experiments to improve survivors' neurological outcomes, the instant inventors discovered that neurological injury could not be attributed to lack of blood flow during CPR since the new method was able to provide 4-8 times higher flow than that achieved with standard CPR. As such, it was hypothesized that a large part of the observed neurologic injury was likely due to the abrupt re-introduction of blood flow. Consequently, and for the first time in cardiac arrest research, IPC was introduced in the form of four 20-second pauses during the initial 3 minutes of CPR, followed by optimal uninterrupted "enhanced" CPR.

Methods—Rationale for Specific IPC Strategy:

Initially, in animal and human studies, an IPC strategy of 3-5 cycles of 15-30 second pauses at the initiation of reperfusion after coronary occlusion and focal or global cerebral ischemia was shown to significantly decrease myocardial and neuronal injury. During primary coronary intervention for STEMI, peak CK-MB was significantly lower in patients with 4 balloon inflations than in those with ≤2 inflations, and there was a positive correlation between LV function and the number of balloon inflations. Although there are limitations on the effectiveness of IPC in the setting of diabetes, obesity, and other co-morbidities, its overall effect has been shown clinically in heterogeneous groups and warrants further investigation in resuscitation science. On the basis of these findings, four, 20-second pauses were introduced during the first 3 min of CPR to provide the maximum combined cerebral and cardiac protection.

Results:

The introduction of IPC drastically changed the neurological outcomes in an animal model. The effect of CPR pauses was profound and occurred even when different CPR methods were used (ACDCPR+ITD) (FIG. 1.) The most striking observation is that the brain demonstrated the potential for full recovery after 15 min of global no-flow ischemia. In contrast, Shaffner et al. reported that cerebral recovery was not feasible after 12 min of untreated arrest because regeneration of ATP was not possible, despite high cerebral perfusion pressures. The instant data suggest otherwise, and is believed to be the first time survival rates with consistently favorable neurological outcomes have been reported after 15 min of untreated cardiac arrest using a non-invasive approach.

Implications:

These preliminary findings suggest IPC can be widely applied at the first responder level during Basic Life Support, with clear implications for more than 70% of U.S. patients who do not receive bystander CPR. Also, the positive effect of the systemically administered nitric oxide (NO) donor SNP suggests an NO-mediated benefit for protection against RI in multiple organs.

Example 2

Cardiac and Neurologic Benefit of IPC (Four 20-Second Pauses) During First 3 Minutes of Standard CPR.

Upon discovering that consistent cardiac recovery with good neurological function is possible after 15 min of untreated cardiac arrest (despite contrary evidence), the instant inventors aimed to identify which components of the above method were most crucial for improved outcome. It was hypothesized that four 20-second pauses during the first 3 minutes of Standard CPR (SCPR would improve post-resuscitation cardiac and neurological function in a porcine model of prolonged untreated cardiac arrest, without compromising ROSC rates.

Methods:
Porcine Model of Cardiac Arrest and Resuscitation.
Briefly, after intubation and instrumentation has been completed, anesthesia with propofol is stopped for 8 min prior induction of VF. Subsequently, ventilation is stopped and VF is left untreated for 15 min. With this protocol the instant inventors have achieved >90% successful ROSC for control animals and their 24-hr survival rate is 50%, with all animals suffering from severe neurological dysfunction or coma. ROSC rates are similar or higher with the proposed strategies so a valid comparison is possible in each preselected time point over the 1-12 hour period after ROSC.

Figure 2:
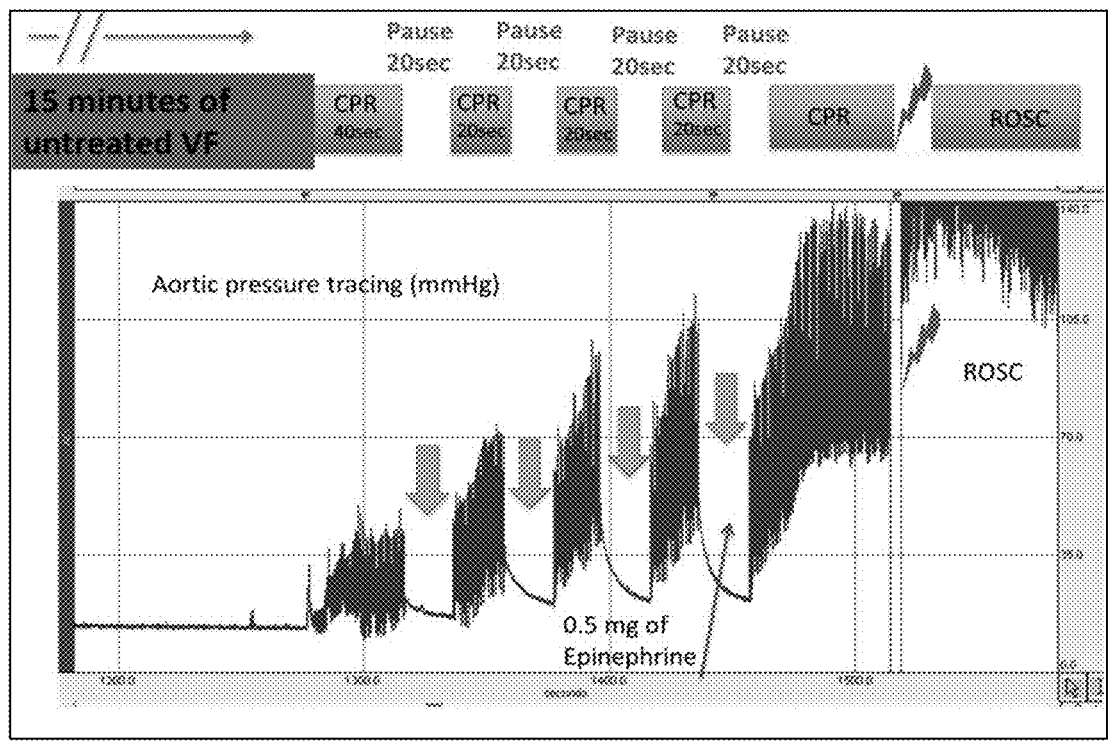
FIG. 2 shows a "stuttering" introduction of reperfusion with SCPR+IPC. During the first 3 min of SCPR, animals received four 20-second pauses and each pause was followed by 20 seconds of SCPR. The "stuttering" introduction of reperfusion is shown. VF: ventricular fibrillation; ROSC: return of spontaneous circulation.

18 pigs had 15 min of untreated VF and were randomized to receive either IPC with four, controlled, 20-sec pauses during the first 3 min of Standard CPR (SCPR+IPC) or just SCPR (FIG. 2) Resuscitated animals had echocardiographic evaluation of their left ventricular ejection fraction (LVEF) after 1 and 4 hrs and a blinded neurological assessment with a cerebral performance category (CPC) score assigned at 24 and 48 hrs (1, normal; 2, slightly disabled; 3, severely disabled but conscious; 4, vegetative state).

Results:
Compared to SCPR animals, SCPR+IPC animals had significant improvements in all of the following: LVEF at 1 and 4 hrs (59±11% vs 35±7%; 55±8% vs 31±13%, respectively; $p<0.01$); neurological function at 24 hrs (CPC: 2.7±0.4 vs 3.8±0.4, respectively, $p=0.003$); and neurological function at 48 hrs, with a favorable decrease in mean CPC score from 2.7±0.4 to 1.7±0.4 ($p<0.001$).

Implications:
IPC with four 20-sec pauses during the first 3 min of SCPR improved post-resuscitation cardiac function and facilitated neurological recovery after 15 min of untreated cardiac arrest in pigs. These latter findings suggest that IPC with introduction of pauses at the initiation of CPR might be more important therapy at the beginning of reperfusion than the CPR method itself.

Example 3

Effects of IPC During SCPR on Cerebral Histopathology, Cardiac Biomarkers, and LV Function.

Given the significantly improved outcomes when IPC was added to SCPR, it was next sought to investigate the effect of IPC on cerebral histology at 48 hrs post ROSC and on blood levels of cardiac troponin I (cTnI) and CK-MB at 4 hrs post resuscitation as further evidence of RI protection. After 15 min of untreated VF, 20 animals were randomized to receive either SCPR alone or SCPR+IPC. All animals had ROSC and received 12-hr intensive care. Animals that were found dead without direct observation were excluded from histological analysis due to unknown time of death. At 48 hrs (or if the veterinarian decided that the animals needed to be sacrificed after the 24-hr evaluation) animals were sacrificed for immediate brain harvest (6 brains from the SCPR group, 10 from the IPC+SCPR group). Average time of harvest was shorter for the SCPR group than for the IPC group (20±12 vs 39±12 hrs, respectively) since the animals either died earlier or were in coma and had to be sacrificed per IACUC protocol.

Histopathological evaluation with hematoxilin and eosin stain for ischemia of the brain was performed by a pathologist blinded to treatment group in all animals. A semi-quantitative scale of ischemic injury was used with the H&E staining of formaldehyde preserved brains. Eight cerebral regions were analyzed and graded on a 0-4 scale (0: no injury, 1 to 4, mild to severe). Scores from each region were added to provide a total cerebral histological score (CHS) for each animal (higher scores=more injury).

Results (Table 1):
At 4 hrs post ROSC, the SCPR+IPC group had a significantly higher LVEF and lower blood levels of CKMB and cTnI than SCPR controls. In addition, histological evaluation of brains at 48 hrs revealed a significant decrease in cerebral ischemic injury (measured by CHS) in the IPC group compared to SCPR controls. Most of the injury was observed in the putamen and hippocampus areas. All 10 animals that received IP, showed mild or no injury, leading to a significant decrease in the total CHS. In that group, 3 animals demonstrated complete absence of ischemic injury and a CHS of 0. IPC significantly decreased mortality at 48 hrs compared to SCPR (hazard ratio: 0.2±0.1, CI: 0.05-0.7, $p=0.01$).

TABLE 1

Cardiocerebral protection during SCPR +/− IPC

| Outcome | SCPR + IPC | SCPR controls | P-value |
| --- | --- | --- | --- |
| LVEF | 59 ± 11% | 33 ± 9% | p < 0.01 |
| CKMB (ng/mL) | 13 ± 10 | 37 ± 24 | p < 0.05 |
| cTnI (ng/mL) | 8.5 ± 7 | 31 ± 34 | p < 0.05 |
| Total CHS | 4 ± 2 | 10 ± 2 | p < 0.01 |

Implications:
For the first time in CPR research, these results associate IPC with direct evidence of end organ protection by utilizing more sensitive and direct measures of decreased injury of the vital organs. Furthermore they associate the observed benefits to functional clinical outcomes. Histopathology and biomarkers of injury are used as endpoints throughout the proposed studies.

Example 4

Preliminary Evaluation of IAPC Combined with SCPR after Prolonged Cardiac Arrest.

Six animal experiments were conducted in which inhaled sevoflurane was administered at the initiation of CPR. Initial anesthesia was performed with propofol and discontinued 8 min before induction of VF. VF was left untreated for 15 min. At the initiation of SCPR, inhaled sevoflurane at 3% was administered via the anesthesia machine for a total of 3 min. Control animals did not receive sevoflurane during CPR. After ROSC was achieved, sevoflurane was restarted at 0.6-0.8% as per IACUC protocol for anesthesia in all animals in both groups.

Figure 3:
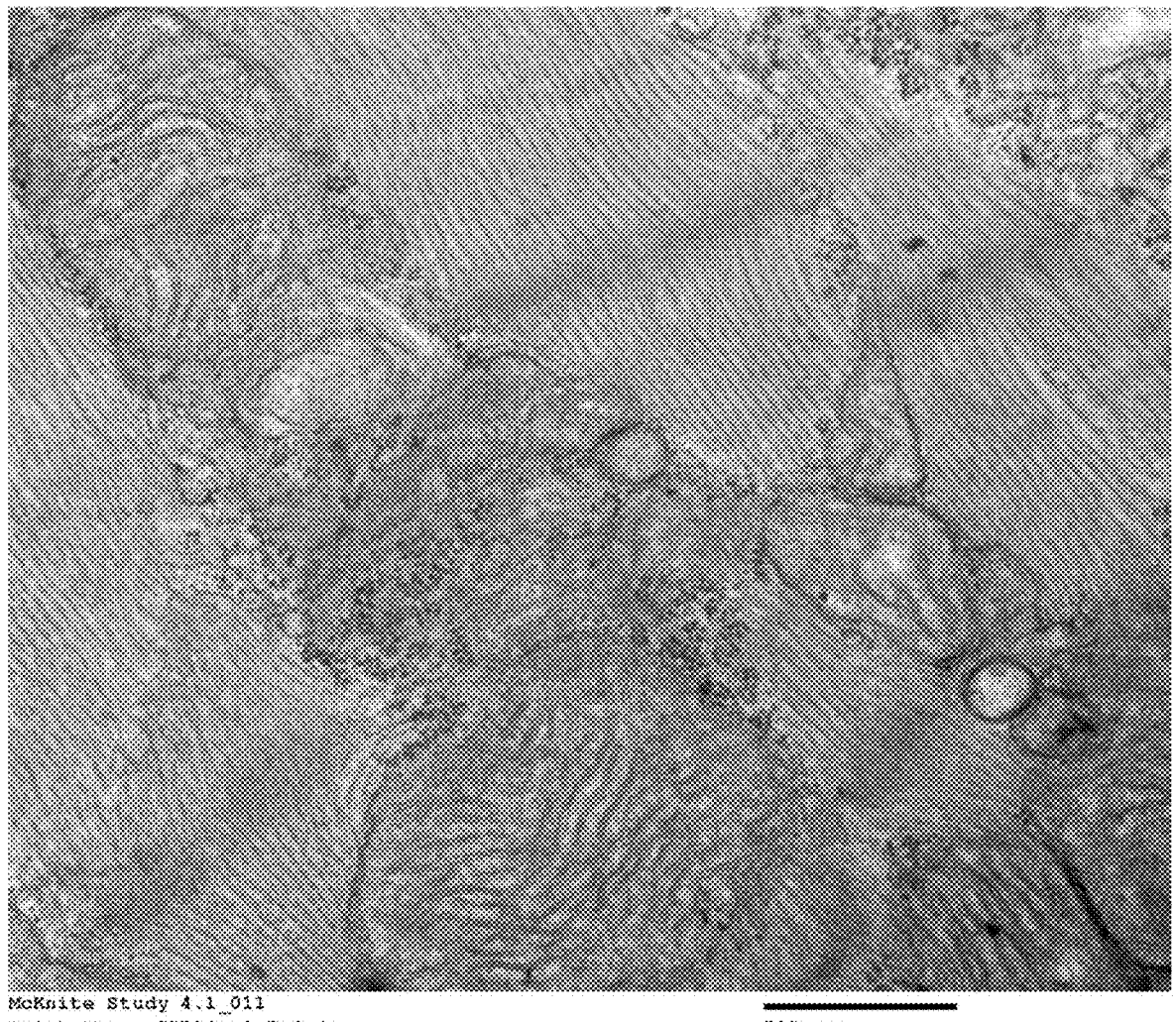
FIG. 3 is a LV septal myocardial biopsy obtained 4 hrs after ROSC, showing intact mitochondrial structure with electron microscope after 15 min of untreated VF arrest followed by 3% sevoflurane introduction at the initiation of CPR.

Results:

In all six IAPC treated animals, ROSC was achieved with 1-2 defibrillations after 4 min CPR and one dose of 0.5 mg of epinephrine. Cardiac function after 1 and 4 hrs was normal (EF=58±12% and 63±8%), and post-resuscitation inotropic support was unnecessary due to the absence of hemodynamic instability. 2/6 animals had undetectable levels and 4/6 animals had mild elevation of CKMB and cTnI at 4 hrs post-ROSC (6.8±9 and 5.8±11 in ng/mL, respectively). In the 10 control SCPR animals, post-ROSC LV function was severely compromised (EF=33±9%) and there was significant elevation of CKMB and cTnI at 4 hrs post-ROSC (37±24 and 31±34 p<0.05). The cerebral effects have not been fully evaluated in the IAPC group. In 4 IAPC animals, myocardial septal left ventricular biopsies were obtained at 4 hours after ROSC and were sent to our core laboratory for electron microscopy Mitochondrial structure appeared normal without evidence of swelling or structural degradation (FIG. 3).

Implications:

Based on these results, it appears that IAPC in this severe model of prolonged cardiac arrest may provide global systemic protection. Accordingly, it may be possible to utilize a simple mobile device that can deliver a bolus of gas of known concentration for the first 3-5 min of CPR via either an endotracheal tube, facemask or a supraglottic device.

Example 5

Effects of Combining IPC or IAPC with Post Resuscitation TH.

In the majority of animal experiments that involved survival after 15 min of untreated arrest, post-ROSC mild TH from 4-12 hrs was utilized. In an analysis of 82 animals resuscitated after 15 min of cardiac arrest, the duration of TH, time to target temperature after ROSC, and rate of rewarming showed no correlation with cerebral performance category score ($r^2<0.4$ for all). In the instant inventors experience, animals treated with SCPR without TH cannot be sustained alive for 24 hrs. Addition of TH provides the ability to increase 24-hr survival rates to 30-40%, but neurological function is poor and animals are unable to walk, stand, and drink. All animals appear moderately to severely impaired with neurological deficits, seizures, depressed LV function, and respiratory failure.

The introduction of IPC in addition to TH provides almost >80% 24-hr survival, with 40-50% of the animals being scored in the favorable neurological category at 48 hrs (CPC<3). Perhaps most intriguing, the absence of TH in a small group of 4 animals that were treated with IPC led to no observable differences in outcomes; 3/4 animals had a CPC<3. Furthermore, all 6 animals that received IAPC with sevoflurane in the absence of TH had remarkable recovery of their cardiac function, and 4/6 animals scored a CPC of 1 and 2 at 24 hrs.

Implications:

If early application of postconditioning during CPR optimizes the chances for recovery and provides a healthier biological substrate to the post cardiac arrest period, it is possible that the benefits of TH may be mitigated or the need for TH may be much shorter in duration and limited to avoiding a post resuscitaiton raise of core temperature.

Discussion of Examples 1-5

The Examples above demonstrated, for the first time, that a strategy of controlled reperfusion (IPC) after prolonged global ischemia in cardiac arrest exhibits the same benefits for the myocardium as seen in other cardiology applications (e.g. during ST elevation myocardial infarction), and specifically mitigates the post-resuscitation cardiac dysfunction that contributes significantly to post-resuscitation morbidity and mortality. Additionally, preliminary evidence of decreased levels of cardiac biomarkers of injury and ischemic brain injury were obtained in histopathological analysis, complementing the findings of improved neurological function and survival at 24/48 hrs. Furthermore, a possible interaction between postconditioning during CPR and the effectiveness of TH post resuscitation was identified.

Example 6

Coronary and Myocardial Function Evaluation.

Reactive oxygen species (ROS) such as $O_2^-$, $H_2O_2$, and $ONOO^-$ are small, highly reactive molecules that have both physiological and pathological effects on myocardial and vascular function. The burst of ROS that occurs during reperfusion following ischemia is a main contributor to coronary and cardiomyocyte dysfunction. Both structural and functional abnormalities of the coronary microvasculature occur that can limit blood flow during reperfusion despite the presence of patent epicardial coronary arteries. Mechanical obstruction of the microvessels by intraluminal endothelial protrusions or blebs, or by swollen cardiomyocytes that compress the microvessels, can limit maximal coronary flow rates or if severe, can cause absolute reductions of coronary flow ("no reflow phenomenon"). More subtle injury can result in endothelial dysfunction in which vasodilator responses that depend on endothelial production of vasodilators such as nitric oxide are impaired.

Figure 4:
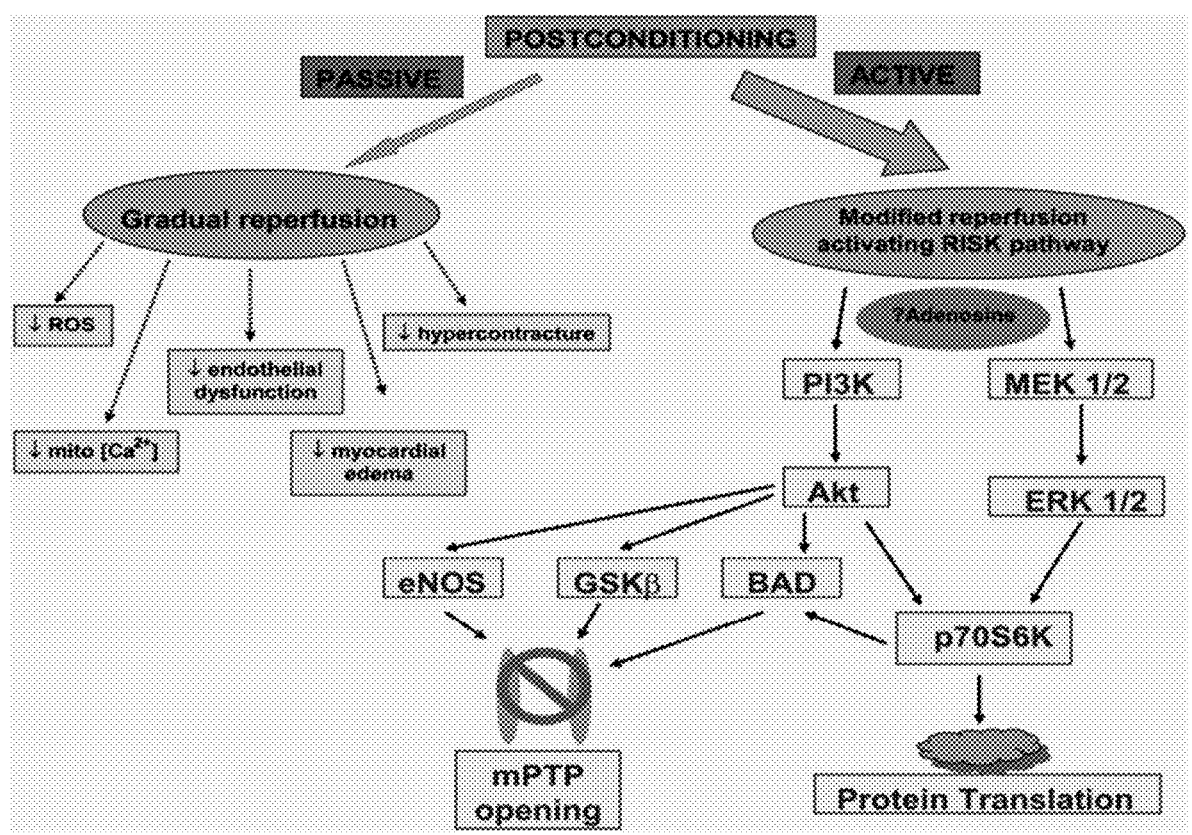
FIG. 4 shows a hypothetical scheme showing the possible mechanisms of protection induced by ischemic postconditioning during acute myocardial infarction: 1) gradual reperfusion may have a "passive" effect modifying reperfusion injury by a reduction in ROS, mitochondrial calcium load (mito [$Ca^{2+}$]), endothelial dysfunction, myocardial edema, and hypercontracture; or 2) upregulation of the reperfusion injury salvage kinase (RISK) pathway, an "active" effect via activation of phosphatidylinositol 3-kinase (PI3K)-Akt or ERK ½, phosphorylates downstream targets such as glycogen synthase kinase-3β (GSK-β), BAD/Bax, and endothelial (NO) synthase (eNOS), producing NO, which inhibits mitochondrial permeability transition pore (mPTP) opening. Phosphorylation of p70s6K confers protection by inactivating BAD or through protein translation." Adapted from reference number 41.
Figure 5:
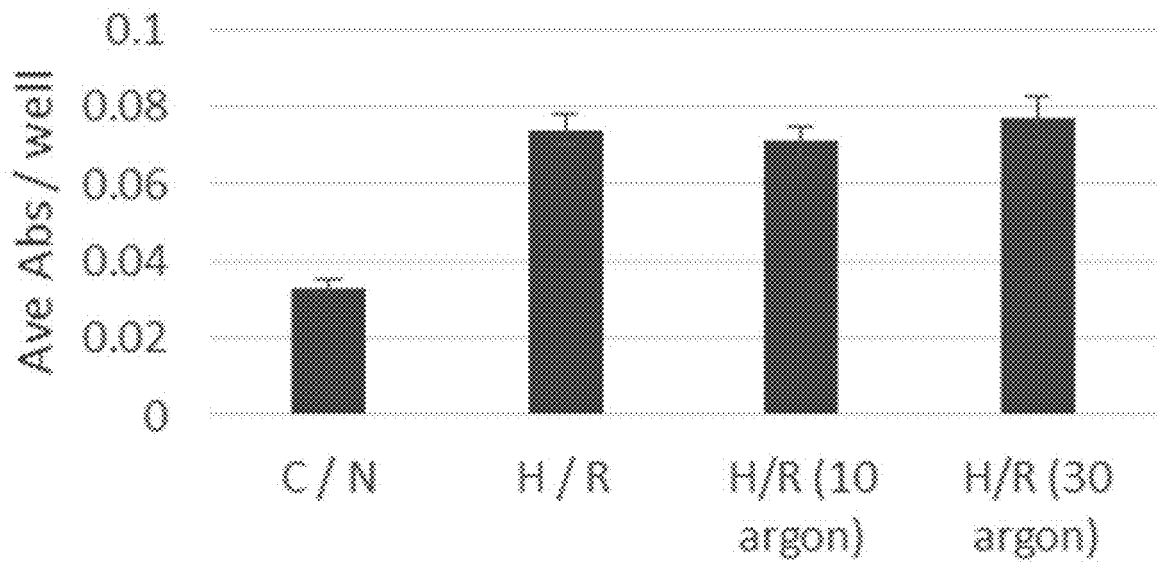
FIG. 5 shows graphs illustrating results of isolated cell experiments in human cardiomyocytes (upper panel) and coronary artery endothelial cells (lower panel). These experiments show no evidence that Argon, given for 10 min or 30 min upon reoxygenation (R) after hypoxia (H), directly improves the cellular injury marker lactate dehydrogenase (LDH) compared to control HR with nitrogen.
Figure 5:
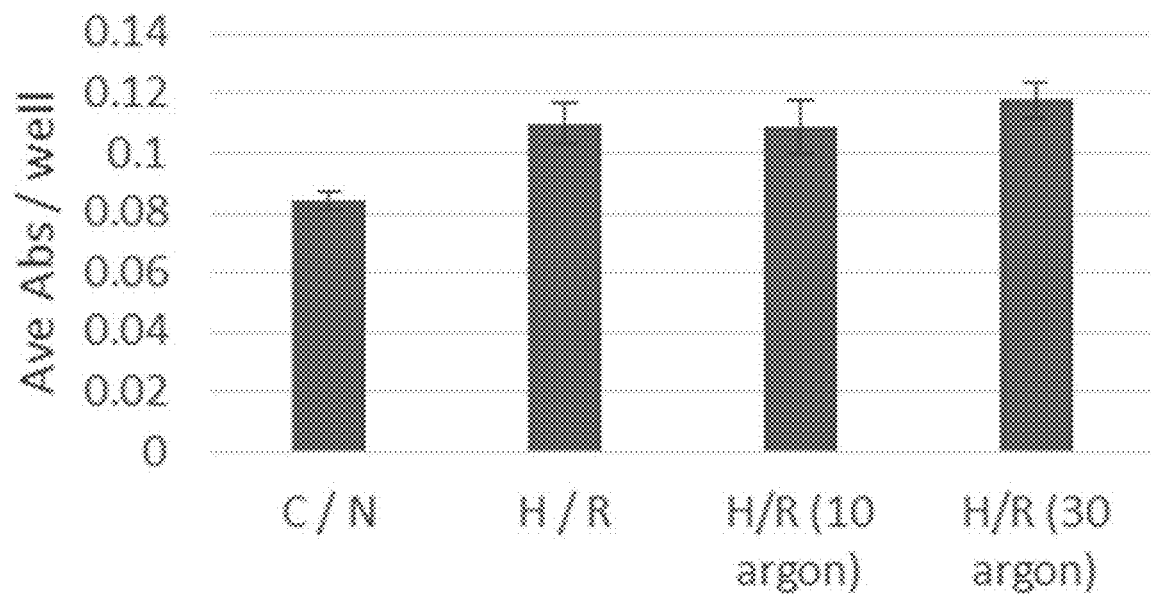
Figure 6:
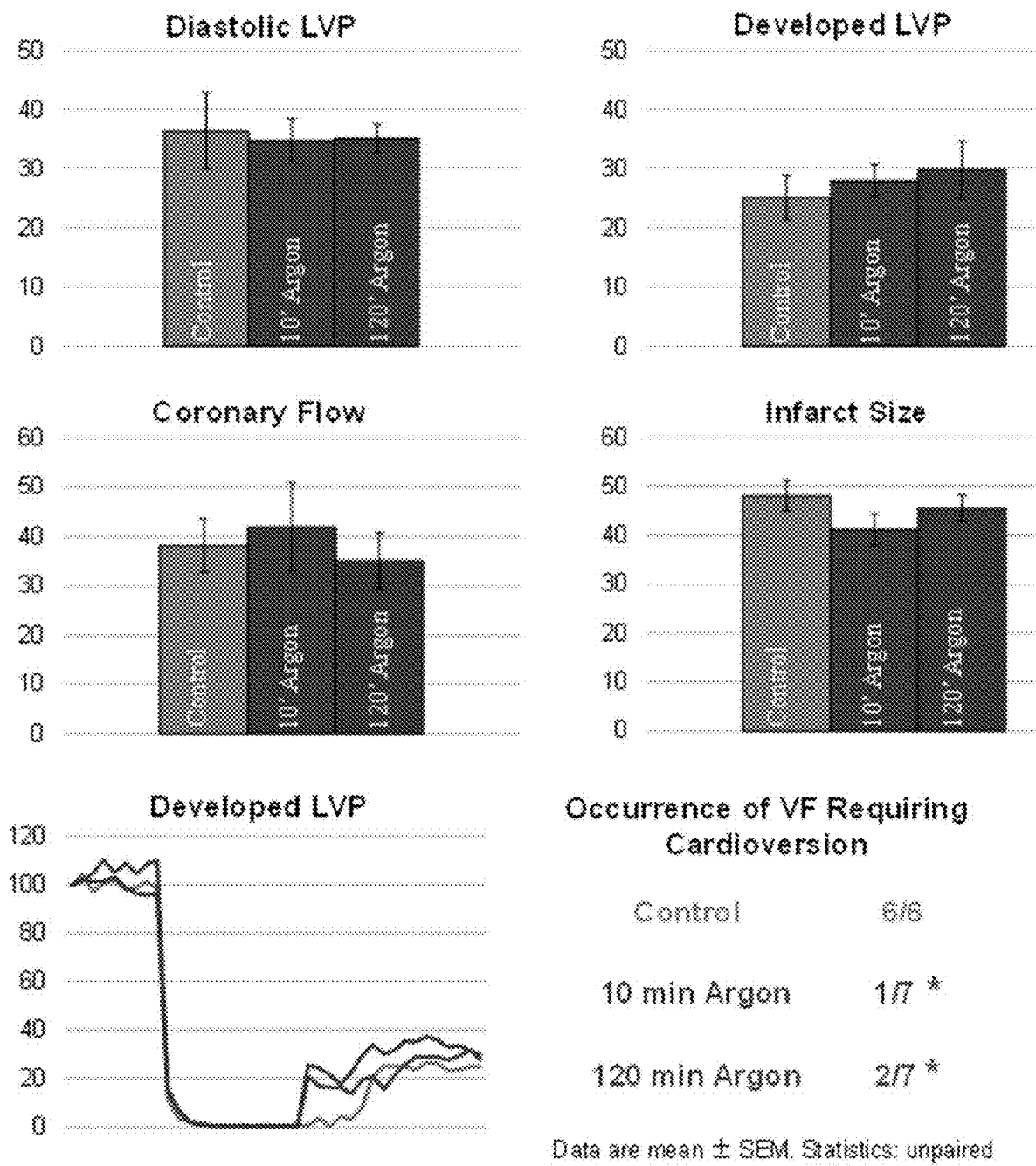
FIG. 6 shows graphs illustrating that there was no evidence of improved infarct size, coronary or myocardial function as assessed by diastolic and developed (systolic minus diastolic) left ventricular pressure (LVP), coronary flow in rat isolated hearts undergoing 30 min global no-flow ischemia and 120 min reperfusion in the presence of 65% Argon for 10 or 120 min compared to 65% Nitrogen (control). Argon hearts, however, required significantly less, defibrillation by lidocaine administration than control hearts to convert back to sinus rhythm. *P<0.05.
Figure 7:
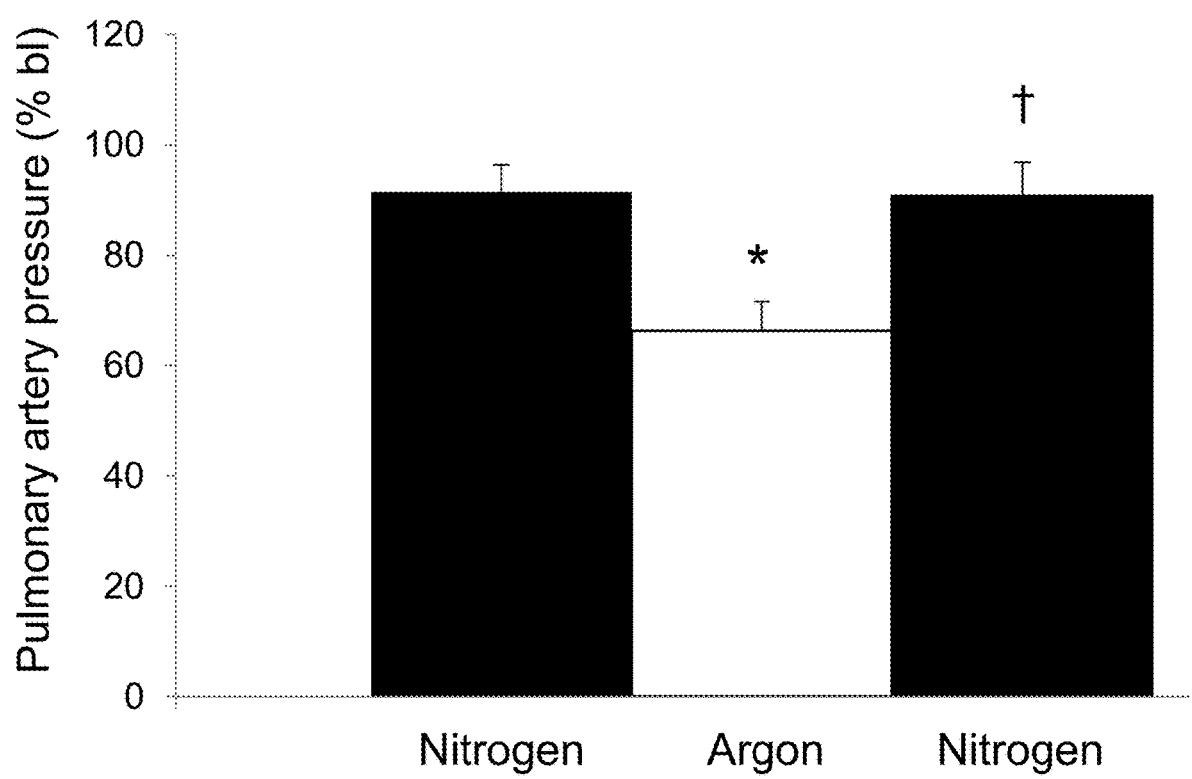
FIG. 7 shows a graph illustrating the effect of difference gas mixtures on pulmonary vascular resistance. Rat isolated lungs ventilated with either 65% $N_2$ or 65% Argon plus 30% $O_2$ and 5% $CO_2$ and perfused at a rate of 40 mL/kg body weight with physiological salt solution plus 4% albumin via cannulas placed into the pulmonary artery (PA) and left atrium. PA pressure is recorded throughout the experiment and analyzed to determine the effect of different gas mixtures on the pulmonary vascular resistance. Argon led to a reversible 28% drop in pulmonary perfusion pressure at constant flow compared to ventilation with Nitrogen before and after. $P<0.05$*vs Nitrogen, † vs Argon.
Figure 8:
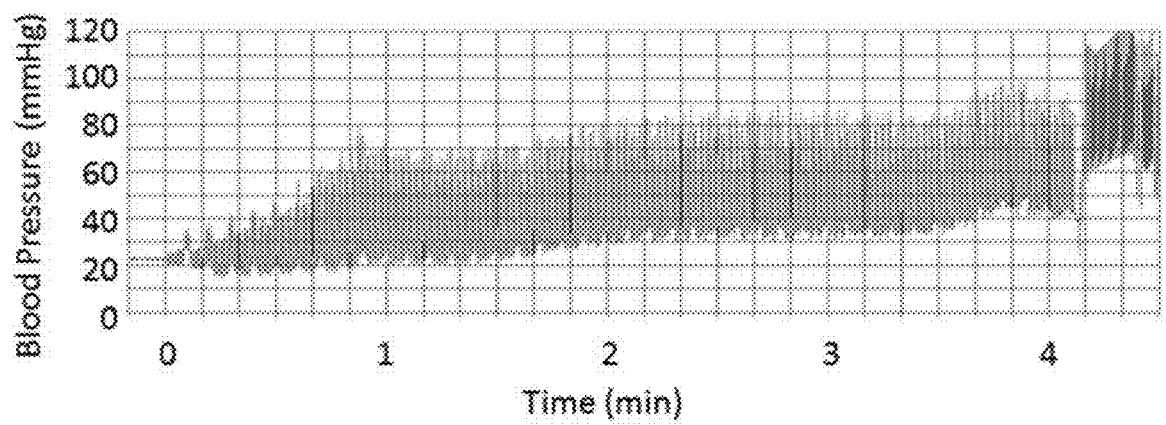
FIG. 8 shows graphs and tables illustrating samples of arterial pressure tracings during identical automated chest compressions in 40-kg female Yorkshire pigs treated with Argon/$O_2$ (2 top panels) or Nitrogen/$O_2$ (2 bottom panels; y-axes adjusted to same mmHg) for 4 min before defibrillation and return of spontaneous circulation (ROSC). Argon treatment led to higher systemic pulse pressures (arterial pressure during compression minus pressure during decompression), a lower number of defibrillation attempts and epinephrine requirements to achieve ROSC, a higher ROSC rate, lower lactic acidosis upon ROSC and lower cardiac injury markers (CK-MB and Troponin I) 6 hours after ROSC.
Figure 8:
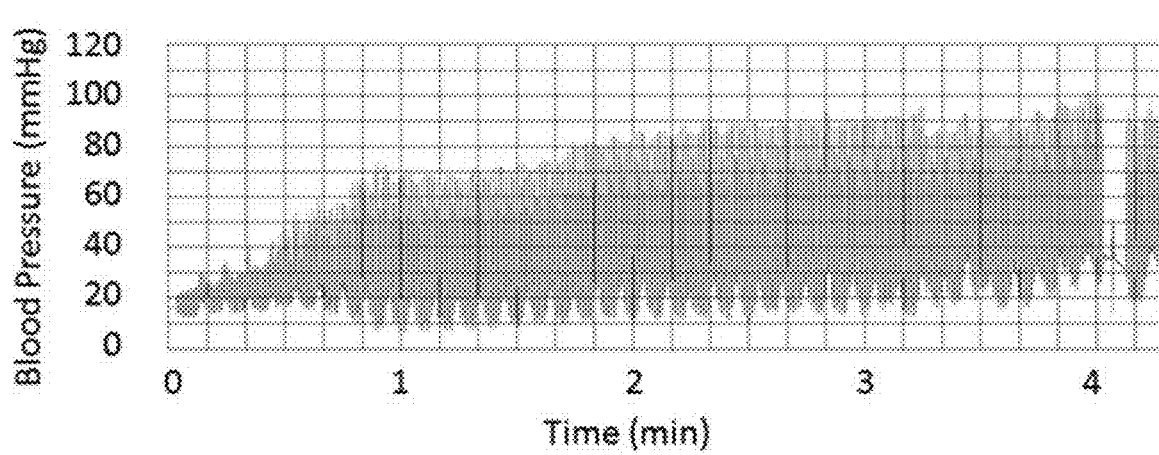

The impairment of endothelium dependent vasodilation is, at least in part, the result of damage caused by oxygen radicals generated during reperfusion and are improved by antioxidants administered immediately prior to reperfusion. In the cardiomyocytes transient opening of the mitochondrial permeability transition pore (mPTP) can produce reversible cellular changes that are involved in normal physiological processes and in fact can contribute to cardioprotection. However, the loss of mitochondrial membrane potential and matrix swelling caused by more prolonged mPTP opening are central to ischemia/reperfusion injury. Oxidative stress that results in prolonged opening of the mPTP during reperfusion results in profound changes of cellular bioenergetics with collapse of the mitochondrial membrane potential and inability of the F0F1-ATPase to generate ATP. The subsequent matrix swelling causes rupture of the outer mitochondrial membrane with release of proapoptotic proteins including Cytochrome c from the intermembrane space into the cytosol which leads to activation of caspase-mediated apoptosis. For these reasons "passive" and "active" mechanisms of protection post resuscitation are evaluated according to FIG. 4:

Collection and evaluation of blood and cerebrospinal fluid in connection with "passive" and "active" mechanisms of protection in the global systemic state of cardiac arrest and CPR induced reperfusion includes regular collection of standardized arterial and venous blood gasses, as well as collection of cerebrospinal fluid at the time of euthanization. The cerebrospinal fluid is then evaluated by Western blot and ELISA for mechanistic biomarkers (calpain-cleaved α-spectrin and caspase-cleaved α-spectrin, cytochrome C, F2-isoprostanes) as well as markers of neuronal injury (neuron specific enolase (NSE), hyperphosphorylated neurofilament, 14-3-3β).

Histopathology in connection with "passive" and "active" mechanisms of protection in the global systemic state of cardiac arrest and CPR induced reperfusion may be performed as follows. (a) Endomyocardial biopsies are taken with standard human techniques under direct fluoroscopic guidance. Fresh samples are evaluated for myocardial edema and mitochondrial integrity.

(b) Fresh brain biopsies (two) are taken from the frontal cortex for mitochondrial analysis and biochemical analysis immediately before euthanization. The first biopsy is snap frozen and subsequently processed for Western blot analysis of post-conditioning pathways (p-PKB, p-AKT, p-GSK-3β, p☐eNOS) and neuronal injury mechanisms (calpain-cleaved α-spectrin, caspase-cleaved α-spectrin). The second biopsy is immediately fractionated to isolate mitochondria for functional analysis.

(c) Formalin perfusion fixed brains are sliced coronally with the initial cut at the level of the mammillary bodies and additional cuts at 1 cm intervals. Reproducible tissue blocks (1 $cm^3$) from standardized five regions of the brain are cryoprotected and frozen. Each block is serially sectioned (50 μm) and all sections stored in cryoprotectant. Every 10th section is processed for immunohistochemistry or H&E stain. Neurons are immunolabeled with the neuron-specific marker NeuN, and co-labeled for markers of injury (calpain-cleaved α-spectrin, caspase-cleaved α-spectrin) or post-conditioning (p-PKB, phospho-AKT and phospho-GSK-3). Immunolabeled neurons are quantified by stereology at 1, 4, 8, and 12 hours after cardiac arrest. Normal H&E stained neurons and injured neurons labeled with FlouroJade B are quantified by stereology at 48 hours after cardiac arrest in the survival studies.

Example 7

So far, Argon has not been used immediately upon reperfusion, i.e. at the beginning of CPR, and its potential mechanisms of organ protection are unknown. Based on a variety of experiments in vitro, ex vivo, and in vivo presented below (FIGS. 5-8 and Table 2), it is postulated that 70% Argon, given immediately upon reperfusion/reoxygenation, improves CPR after CA by two distinct mechanisms: 1) a profound antiarrhythmic effect, evidenced in isolated hearts (ex vivo: less ventricular fibrillation requiring defibrillation by lidocaine) and whole animals (in vivo: less shocks necessary to defibrillate); and 2) increased cardiac output likely due to reversible pulmonary vaso-relaxation and subsequently increased cardiac stroke volume during CPR, evidenced in isolated lungs (ex vivo: lower pulmonary artery pressure at constant flow) and whole animals (in vivo: higher pulse pressure during CPR).

TABLE 2

|  | 70% Nitrogen/ 30% Oxygen | 70% Argon/30% Oxygen |
| --- | --- | --- |
| Pulse pressure at 3 min CPR (mmHg) | 40.4 ± 3.9 | 62.3 ± 3.7 |
| ROSC (%) | 80 | 100 |
| Number of defibrillations to achieve ROSC (n) | 6.4 ± 1.9 | 2.4 ± 1.0 |
| Epinephrine dose to achieve ROSC (mg) | 1.3 ± 0.2 | 0.7 ± 0.2 |
| Arterial pH upon ROSC | 6.98 | 7.27 ± 0.05 |
| Lactate upon ROSC (mEq) | 15.0 | 6.8 ± 0.7 |
| CK-MB 6 hrs after ROSC (ng/mL) | 44.2 | 15.2 ± 4.3 |
| Troponin I 6 hrs after ROSC (ng/mL) | 178.2 | 6.8 ± 4.7 |

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Nichol G, Soar J: Regional cardiac resuscitation systems of care. Curr Opin Crit Care 2010; 16: 223-30. PMID: 20463465.
2. Bottiger B W, Van Aken H K: Saving 100,000 lives each year in Europe. Best Pract Res Clin Anaesthesiol 2013; 27: 291-2. PMID: 24054507.
3. Kalogeris T, Bao Y, Korthuis R J: Mitochondrial reactive oxygen species: a double edged sword in ischemia/reperfusion vs preconditioning. Redox Biol 2014; 2: 702-14. PMID: 24944913.
4. Zhao Z Q, et al. Inhibition of myocardial injury by ischemic postconditioning during reperfusion: Comparison with ischemic preconditioning. Am J Physiol Heart Circ Physiol. 2003; 285:H579-588
5. Zhao H. Ischemic postconditioning as a novel avenue to protect against brain injury after stroke. J Cereb Blood Flow Metab. 2009; 29:873-885
6. Bernard S A, et al. Treatment of comatose survivors of out-of-hospital cardiac arrest with induced hypothermia. N Engl J Med. 2002; 346:557-563
7. Segal N, Matsuura T, Caldwell E, Sarraf M, McKnite S, Zviman M, Aufderheide T P, Halperin H R, Lurie K G, Yannopoulos D: Ischemic postconditioning at the initiation of cardiopulmonary resuscitation facilitates functional cardiac and cerebral recovery after prolonged untreated ventricular fibrillation. Resuscitation 2012; 83: 1397-403. PMID: 22521449.
8. Strategies to Improve Cardiac Arrest Survival: A Time to Act. Institute of Medicine 2015.
9. Aufderheide T P, et al. Standard cardiopulmonary resuscitation versus active compression-decompression cardiopulmonary resuscitation with augmentation of negative intrathoracic pressure for out-of-hospital cardiac arrest: A randomised trial. Lancet. 2011; 377:301-311.
10. Yellon D M, et al. Myocardial reperfusion injury. N Engl J Med. 2007; 357:1121-1135.
11. Staat P, et al. Postconditioning the human heart. Circulation. 2005; 112:2143-2148.
12. Gateau-Roesch O, et al. Mitochondrial permeability transition pore and postconditioning. Cardiovasc Res. 2006; 70:264-273.
13. Murphy E, et al. What makes the mitochondria a killer? Can we condition them to be less destructive? Biochim Biophys Acta. 2011; 1813:1302-1308.
14. Piot C, et al. Effect of cyclosporine on reperfusion injury in acute myocardial infarction. N Engl J Med. 2008; 359:473-481.
15. Cour M, et al. Inhibition of mitochondrial permeability transition to prevent the post-cardiac arrest syndrome: A pre-clinical study. Eur Heart J. 2011; 32:226-235.

16. Chen D, et al. The effect of sevoflurane postconditioning on cardioprotection against ischemia-reperfusion injury in rabbits. *Mol Biol Rep.* 2012; 39:6049-6057.
17. Meybohm P, et al. Pharmacological postconditioning with sevoflurane after cardiopulmonary resuscitation reduces myocardial dysfunction. *Crit Care.* 2011; 15:R241.
18. Rohilla A, et al. Myocardial postconditioning: Next step to cardioprotection. *Arch Pharm Res.* 2011; 34:1409-1415.
19. Oei G T, et al. Cellular effects of helium in different organs. *Anesthesiology.* 2010; 112:1503-1510.
20. Wang J K, et al. Postconditioning with sevoflurane protects against focal cerebral ischemia and reperfusion injury via pi3k/akt pathway. *Brain Res.* 2010; 1357:142-151.
21. Meybohm P, Gruenewald M, Albrecht M, Müller C, Zitta K, Foesel N, Maracke M, Tacke S, Schrezenmeir J, Scholz J, Bein B: Pharmacological postconditioning with sevoflurane after cardiopulmonary resuscitation reduces myocardial dysfunction. Crit Care 2011; 15: R241. PMID: 22011328.
22. Riess M L, Matsuura T R, Bartos J A, Bienengraeber M, Aldakkak M, McKnite S H, Rees J N, Aufderheide T P, Sarraf M, Neumar R W, Yannopoulos D: Anaesthetic Postconditioning at the Initiation of CPR Improves Myocardial and Mitochondrial Function in a Pig Model of Prolonged Untreated Ventricular Fibrillation. Resuscitation 2014; 85: 1745-51. PMID: 25281906.
23. Bartos J A, Matsuura T R, Sarraf M, Youngquist S T, McKnite S H, Rees J N, Sloper D T, Bates F S, Segal N, Debaty G, Lurie K G, Neumar R W, Metzger J M, Riess M L, Yannopoulos D: Bundled postconditioning therapies improve hemodynamics and neurologic recovery after 17 min of untreated cardiac arrest. Resuscitation 2015; 87: 7-13. PMID: 25447036.
24. Brücken A, Cizen A, Fera C, Meinhardt A, Weis J, Nolte K, Rossaint R, Pufe T, Marx G, Fries M: Argon reduces neurohistopathological damage and preserves functional recovery after cardiac arrest in rats. Br J Anaesth 2013; 110 Suppl 1: i106-12. PMID: 23393152.
25. Brücken A, Kurnaz P, Bleilevens C, Derwall M, Weis J, Nolte K, Rossaint R, Fries M: Dose dependent neuroprotection of the noble gas argon after cardiac arrest in rats is not mediated by KATP-channel opening. Resuscitation 2014; 85: 826-32. PMID: 24582739.
26. Ristagno G, Fumagalli F, Russo I, Tantillo S, Zani D D, Locatelli V, De Maglie M, Novelli D, Staszewsky L, Vago T, Belloli A, Di Giancamillo M, Fries M, Masson S, Scanziani E, Latini R: Postresuscitation treatment with argon improves early neurological recovery in a porcine model of cardiac arrest. Shock 2014; 41: 72-8. PMID: 24088999.
27. Pagel P S: Cardioprotection by noble gases. J Cardiothorac Vasc Anesth 2010; 24: 143-63. PMID: 19467886.
28. Schultz J, et al. Sodium nitroprusside enhanced cardiopulmonary resuscitation prevents post-resuscitation left ventricular dysfunction and improves 24-hour survival and neurological function in a porcine model of prolonged untreated ventricular fibrillation. *Resuscitation.* 2011; 82S: S35-S40.
29. Shaffner D H, et al. Effect of arrest time and cerebral perfusion pressure during cardiopulmonary resuscitation on cerebral blood flow, metabolism, adenosine triphosphate recovery, and ph in dogs. *Crit Care Med.* 1999; 27:1335-1342.
30. Allen B S, et al. Studies of isolated global brain ischaemia: Ii. Controlled reperfusion provides complete neurologic recovery following 30 min of warm ischaemia—the importance of perfusion pressure. *Eur J Cardiothorac Surg.* 2012; 41:1147-1154.
31. Segal N, et al. Ischemic postconditioning at the initiation of cardiopulmonary resuscitation facilitates functional cardiac and cerebral recovery after prolonged untreated ventricular fibrillation. *Resuscitation.* 2012.
32. Yannopoulos D, et al. Controlled pauses at the initiation of sodium nitroprusside-enhanced cardiopulmonary resuscitation facilitate neurological and cardiac recovery after 15 mins of untreated ventricular fibrillation. *Crit Care Med.* 2012; 40:1562-1569.
33. Högler S, et al. Distribution of neuropathological lesions in pig brains after different durations of cardiac arrest. *Resuscitation.* 2010; 81:1577-1583.
34. Riess M L, et al. Preconditioning with sevoflurane reduces changes in nicotinamide adenine dinucleotide during ischemia-reperfusion in isolated hearts: Reversal by 5-hydroxydecanoic acid. *Anesthesiology.* 2003; 98:387-395.
35. Kevin L G, et al. Sevoflurane exposure generates superoxide but leads to decreased superoxide during ischemia and reperfusion in isolated hearts. *Anesth Analg.* 2003; 96:949-955, table of contents.
36. Siman R, et al. Novel surrogate markers for acute brain damage: Cerebrospinal fluid levels corrrelate with severity of ischemic neurodegeneration in the rat. *J Cereb Blood Flow Metab.* 2005; 25:1433-1444.
37. Che D, et al. Impact of therapeutic hypothermia onset and duration on survival, neurologic function, and neurodegeneration after cardiac arrest. *Crit Care Med.* 2011; 39:1423-1430.
38. Griffiths C, et al. A new and simple method for delivering clamped nitric oxide concentrations in the physiological range: Application to activation of guanylyl cyclase-coupled nitric oxide receptors. *Mol Pharmacol.* 2003; 64:1349-1356.
39. McAllister S E, et al. Postconditioning for salvage of ischemic skeletal muscle from reperfusion injury: Efficacy and mechanism. *Am J Physiol Regul Integr Comp Physiol.* 2008; 295:R681-689.
40. Stumpner J, et al. Desflurane-induced post-conditioning against myocardial infarction is mediated by calcium-activated potassium channels: Role of the mitochondrial permeability transition pore. *Br J Anaesth.* 2012; 108: 594-601.
41. Tsang A, et al. Myocardial postconditioning: Reperfusion injury revisited. *Am J Physiol Heart Circ Physiol.* 2005; 289:H2-7.
42. Becker L B. New concepts in reactive oxygen species and cardiovascular reperfusion physiology. *Cardiovasc Res.* 2004; 61:461-470.
43. Penna C, et al. Mitochondrial pathways, permeability transition pore, and redox signaling in cardioprotection: Therapeutic implications. *Antioxid Redox Signal.* 2012.
44. Lu Z, et al. Extracellular superoxide dismutase deficiency exacerbates pressure overload-induced left ventricular hypertrophy and dysfunction. *Hypertension.* 2008; 51:19-25.
45. Zhang P, et al. Nadph oxidase contributes to coronary endothelial dysfunction in the failing heart. *Am J Physiol Heart Circ Physiol.* 2009; 296:H840-846.
46. Aldakkak M, et al. Ranolazine reduces ca2+ overload and oxidative stress and improves mitochondrial integrity to protect against ischemia reperfusion injury in isolated hearts. *Pharmacol Res.* 2011; 64:381-392.
47. Gadicherla A K, et al. Damage to mitochondrial complex i during cardiac ischemia reperfusion injury is reduced indirectly by anti-anginal drug ranolazine. *Biochim Biophys Acta.* 2012; 1817:419-429.
48. Heinen A, et al. Reverse electron flow-induced ros production is attenuated by activation of mitochondrial ca2+-sensitive k+ channels. *Am J Physiol Heart Circ Physiol.* 2007; 293:H1400-1407.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating an individual following a period of ischemia, the method comprising:
   administering inhaled agent postconditioning, the inhaled agent comprising at least one non-anesthetic noble gas; and
   performing cardiopulmonary resuscitation simultaneously with the step of administering inhaled agent postconditioning;
   wherein the inhaled agent does not include any volatile anesthetics; and
   wherein the inhaled agent includes at least 50% of the at least one non-anesthetic noble gas.

2. The method of claim 1, wherein the at least one non-anesthetic noble gas is selected from the group consisting of argon, helium, and a combination thereof.

3. The method of claim 1, wherein the at least one non-anesthetic noble gas is a pure noble gas.

4. The method of claim 1, wherein the inhaled agent comprises a mixture of the at least one non-anesthetic noble gas and oxygen.

5. The method of claim 4, wherein the at least one non-anesthetic noble gas is selected from the group consisting of argon, helium, and a combination thereof.

6. The method of claim 4, wherein the mixture of the at least one non-anesthetic noble gas:oxygen ratio of the mixture is 80:20.

7. The method of claim 4, wherein the mixture of the at least one non-anesthetic noble gas:oxygen ratio of the mixture is 70:30.

8. The method of claim 4, wherein the mixture of the at least one non-anesthetic noble gas:oxygen ratio of the mixture is 60:40.

9. The method of claim 4, wherein the mixture of the at least one non-anesthetic noble gas:oxygen ratio of the mixture is 50:50.

10. The method of claim 1, wherein the inhaled agent postconditioning is administered within 15 minutes of the period of ischemia.

11. The method of claim 1, wherein the inhaled agent postconditioning is administered at least 10 minutes after the period of ischemia.

12. The method of claim 1, wherein the inhaled agent postconditioning is administered at least 15 minutes after the period of ischemia.

13. The method of claim 1, wherein the method reduces reperfusion injury following the period of ischemia.

14. The method of claim 1, wherein the non-anesthetic noble gas consists of argon.

15. The method of claim 4, wherein the non-anesthetic noble gas consists of argon.

16. A method to reduce injury of cells after a period of ischemia the method comprising:
    administering non-anesthetic inhaled agent postconditioning; and
    performing cardiopulmonary resuscitation simultaneously with the step of administering non-anesthetic inhaled agent postconditioning;
    wherein the inhaled agent comprises at least one non-anesthetic noble gas;
    wherein the inhaled agent includes at least 50% of the at least one non-anesthetic noble gas; and
    wherein the inhaled agent does not include any volatile anesthetics.

17. The method of claim 16, wherein the cells are myocardial cells.

18. The method of claim 16, wherein the cells are neuronal cells.

19. A method performing cardiopulmonary resuscitation to an individual comprising:
    repeatedly compressing the individual's chest, wherein the chest is compressed during a compression phase followed by a decompression or relaxation phase; and
    simultaneously with the compressing step, administering non-anesthetic inhaled agent postconditioning to the individual receiving cardiopulmonary resuscitation;
    wherein the inhaled agent comprises at least one non-anesthetic noble gas; and
    wherein the inhaled agent includes at least 50% of the at least one non-anesthetic noble gas.

* * * * *